US007910330B2

(12) United States Patent
Kocken et al.

(10) Patent No.: US 7,910,330 B2
(45) Date of Patent: Mar. 22, 2011

(54) **EFFICIENT EXPRESSION OF *PLASMODIUM* APICAL MEMBRANE ANTIGEN IN YEAST CELLS**

(75) Inventors: Clemens Hendricus M. Kocken, Moerkapelle (NL); Alan William Thomas, Boskoop (NL); Michael John Blackman, Hitchin (GB); Chrislaine Withers-Martinez, New Barnet (GB); Anthony Arthur Holder, Mill Hill (GB)

(73) Assignee: Stichting Biomedical Primate Research Centre, Rijswijk (NL)

( * ) Notice: Subject to any disclaimer, the term of this patent is extended or adjusted under 35 U.S.C. 154(b) by 0 days.

(21) Appl. No.: 10/615,615

(22) Filed: Jul. 8, 2003

(65) Prior Publication Data

US 2004/0091971 A1 May 13, 2004

Related U.S. Application Data

(63) Continuation of application No. PCT/NL01/00934, filed on Dec. 21, 2001.

(30) Foreign Application Priority Data

Dec. 22, 2000 (EP) .................................. 00204697

(51) Int. Cl.
*C12N 15/09* (2006.01)
*C12P 21/06* (2006.01)
*C12P 21/04* (2006.01)
(52) U.S. Cl. ................... 435/69.3; 435/69.1; 435/71.1
(58) Field of Classification Search ................. 435/342, 435/7.22, 68.1, 69.1, 69.6, 70.1, 71.1, 471, 435/91.1, 7.1; 424/9.2, 184.1, 151.1
See application file for complete search history.

(56) References Cited

U.S. PATENT DOCUMENTS

2006/0264619 A1* 11/2006 Lanar et al. .................. 536/23.1

FOREIGN PATENT DOCUMENTS

WO        02/052014 A2        7/2002

OTHER PUBLICATIONS

Fandeur et al. Am. J. Trop. Med. 1998; 58(2):225-31.*
Kocken et al. Infect. Immun. Jan. 1999; 67(1):43-49.*
Withers-Martinez et al. Protein Eng. 1999; 12(12):1113-20.*
Michon et al. Mol. Biol. Evol. 2002; 19(7):1128-42.*
EMBL Database Entry PFPF83B, Accession No. M58546, May 1, 1991.
Kocken et al., High-Level Expression of *Plasmodium vivax* Apical Membrane Antigen I (AMA-1) in *Pichia pastoris*: Strong Immunogenicity in *Macaca mulatta* Immunized with *P. vivax* AMA-1 and Adjuvant SBAS2, Infection and Immunity, Jan. 1999, pp. 43-49, vol. 67, No. 1.

Kocken et al., Rapid Screening and Mapping of Conformational Epitopes Expressed in the Secretion Expression System *Pichia pastoris*, Analytical Biochemistry, 1996, pp. 111-112.
Narum et al., Ion-exchange-immunoaffinity purification of a recombinant baculovirus *Plasmodium falciparum* apical membrane antigen, PF83/AMA-1, Journal of Chromatography, 1993, pp. 357-363, vol. 657, Amsterdam.
Thomas et al., Analysis of variation in PF83, an erythrocytic merozoite vaccine candidate antigen of *Plasmodium falciparum*, Molecular and Biochemical Parasitology, 1990, pp. 285-288, vol. 42.
Withers-Martinez et al., PCR-based gene synthesis as an efficient approach for expression of the A + T-rich malaria genome, Protein Engineering, 1999, pp. 1113-1120, vol. 12, No. 12.
PCT International Preliminary Examination Report, PCT/NL01/00934, dated Nov. 1, 2002, 3 pages.
Taylor et al., "Effect of Falciparum Malaria Infection on the in Vitro Mitogen Responses of Spleen and Peripheral Blood Lymphocytes from Owl Monkeys," Am. J. Trop. Med. Hyg., 1978, pp. 738-742, vol. 27, No. 4.
Kocken et al., "High-Level Expression of the Malaria Blood-Stage Vaccine Candidate *Plasmodium falciparum* Apical Membrane Antigen 1 and Induction of Antibodies that Inhibit Erythrocyte Invasion," Infection and Immunity, Aug 2002, pp. 4471-4476, vol. 70, No. 8.
Noonan, Patent Docs: Nature's Unpredictable Thesaurus (visited Mar. 30, 2007) <http://patentdocs.typepad.com/patent_docs/2007/02/natures_unpredi.html>.
Kennedy et al., In Vitro Studies with Recombinant *Plasmodium falciparum* Apical Membrane Antigen 1 (AMA1): Production and Activity of an AMA1 Vaccine and Generation of a Multiallelic Response, Infection and Immunity, Dec. 2002, pp. 6948-6960, vol. 70, No. 12.
Maklin et al., Phase 1 Clinical Trial of Apical Membrane Antigen 1: an Asexual Blood-Stage Vaccine for *Plasmodium falciparum* Malaria, Infection and Immunity, Jun. 2005, pp. 3677-3685, vol. 73, No. 6.

(Continued)

*Primary Examiner* — Nancy Vogel
*Assistant Examiner* — Catherine Hibbert
(74) *Attorney, Agent, or Firm* — TraskBritt

(57) ABSTRACT

A method of efficiently expressing *Plasmodium* AMA-1 ectodomain or a functional part, derivative, and/or analogue thereof, in a eukaryotic expression system. Preferably, the *Plasmodium* AMA-1 ectodomain is Pf AMA-1 ectodomain. This protein may be expressed in yeast, such as *Pichia pastoris*. Efficient expression is possible using a method for producing mRNA encoding the *Plasmodium* AMA-1 ectodomain in a yeast cell, comprising providing the yeast cell with a nucleic acid encoding *Plasmodium* AMA-1 ectodomain, the nucleic acid being modified to utilize the yeast cell's codon usage. Preferably, at least one putative yeast polyadenylation consensus sequence in the nucleic acid has been modified. More preferably, also at least one site in the protein that is generally glycosylated by eukaryotic expression systems, has been removed.

13 Claims, 3 Drawing Sheets

OTHER PUBLICATIONS

Remarque et al., A Diversity-Covering Approach to Immunization with *Plasmodium falciparum* Apical Membrane Antigen 1 Induces Broader Allelic Recognition and Growth Inhibition Response in Rabbits, Infection and Immunity, Jun. 2008, pp. 2660-2670, vol. 76, No. 6.

Crewther et al., Protective Immune Responses to Apical Membrane Antigen 1 of *Plasmodium chabaudi* Involve Recognition of Strain-Specific Epitopes, Infection and Immunity, Aug. 1996, pp. 3310-3317, vol. 64, No. 8.

* cited by examiner

Fig. 1. Synthetic gene for *P. falciparum* FVO strain AMA-1, employing *P. pastoris* codon preference

```
          10        20        30        40        50
ATGAGGAAGTTGTACTGCGTTTTGTTGTTGTCTGCTTTCGAGTTCACCTA
 M  R  K  L  Y  C  V  L  L  L  S  A  F  E  F  T  Y>

60        70        80        90       100
CATGATCAACTTCGGTCGTGGTCAGAACTACTGGGAGCATCCTTACCAGA
 M  I  N  F  G  R  G  Q  N  Y  W  E  H  P  Y  Q>

110       120       130       140       150
AGTCTGACGTCTACCATCCTATCAACGAACATAGGGAGCATCCTAAGGAA
 K  S  D  V  Y  H  P  I  N  E  H  R  E  H  P  K  E>

160       170       180       190       200
TACGAATACCCACTGCATCAAGAGCACACTTACCAGCAGGAAGATTCTGG
 Y  E  Y  P  L  H  Q  E  H  T  Y  Q  Q  E  D  S  G>

210       220       230       240       250
TGAAGATGAAAACACCTTGCAACACGCTTACCCCATCGATCATGAAGGAG
 E  D  E  N  T  L  Q  H  A  Y  P  I  D  H  E  G>

260       270       280       290       300
CTGAACCAGCCCCTCAGGAACAAAACTTGTTCTCTTCCATCGAAATCGTG
 A  E  P  A  P  Q  E  Q  N  L  F  S  S  I  E  I  V>

310       320       330       340       350
GAAAGATCCAACTACATGGGTAACCCATGGACTGAGTACATGGCAAAGTA
 E  R  S  N  Y  M  G  N  P  W  T  E  Y  M  A  K  Y>

360       370       380       390       400
CGACATCGAGGAAGTGCACGGAAGTGGTATCAGGGTTGATCTGGGTGAAG
 D  I  E  E  V  H  G  S  G  I  R  V  D  L  G  E>

410       420       430       440       450
ATGCCGAAGTCGCTGGTACTCAGTACAGACTCCCTTCTGGTAAGTGCCCT
 D  A  E  V  A  G  T  Q  Y  R  L  P  S  G  K  C  P>

460       470       480       490       500
GTTTTCGGAAAGGGTATCATCATCGAAAACTCTAAGACTACTTTCCTCAA
 V  F  G  K  G  I  I  I  E  N  S  K  T  T  F  L  K>

510       520       530       540       550
GCCTGTTGCTACTGGTAACCAAGATCTTAAGGACGGAGGTTTCGCTTTCC
 P  V  A  T  G  N  Q  D  L  K  D  G  G  F  A  F>

560       570       580       590       600
CACCTACTAACCCTCTGATCTCTCCAATGACTTTGAACGGTATGCGTGAC
 P  P  T  N  P  L  I  S  P  M  T  L  N  G  M  R  D>

610       620       630       640       650
TTCTACAAGAACAACGAATACGTCAAGAACTTGGATGAATTGACTTTGTG
 F  Y  K  N  N  E  Y  V  K  N  L  D  E  L  T  L  C>
```

FIG. 1A

```
       660         670         680         690         700
TAGTAGACACGCTGGAAACATGAACCCTGATAACGACAAGAACAGTAACT
  S   R   H   A   G   N   M   N   P   D   N   D   K   N   S   N>

710         720         730         740         750
ACAAGTACCCCGCGGTTTACGACTACAACGATAAGAAGTGTCACATCCTG
  Y   K   Y   P   A   V   Y   D   Y   N   D   K   K   C   H   I   L>

760         770         780         790         800
TACATCGCTGCCCAAGAAAACAACGGACCAAGATACTGTAACAAGGATCA
  Y   I   A   A   Q   E   N   N   G   P   R   Y   C   N   K   D   Q>

810         820         830         840         850
AAGTAAGAGAAACTCTATGTTCTGTTTCAGACCTGCAAAGGACAAGCTGT
  S   K   R   N   S   M   F   C   F   R   P   A   K   D   K   L>

860         870         880         890         900
TCGAAAACTACGTGTACTTGTCCAAGAACGTTGTCGATAACTGGGAAGAA
  F   E   N   Y   V   Y   L   S   K   N   V   V   D   N   W   E   E>

910         920         930         940         950
GTCTGCCCAAGAAAGAACCTCGAGAACGCAAAGTTCGGTCTGTGGGTCGA
  V   C   P   R   K   N   L   E   N   A   K   F   G   L   W   V   D>

960         970         980         990        1000
TGGTAACTGTGAAGACATCCCTCATGTGAACGAGTTCAGTGCTAACGATT
  G   N   C   E   D   I   P   H   V   N   E   F   S   A   N   D>

1010        1020        1030        1040        1050
TGTTCGAGTGTAACAAGCTGGTCTTCGAGTTGTCTGCCAGTGACCAACCT
  L   F   E   C   N   K   L   V   F   E   L   S   A   S   D   Q   P>

1060        1070        1080        1090        1100
AAGCAGTACGAACAGCATTTGACTGACTACGAAAAGATCAAGGAAGGATT
  K   Q   Y   E   Q   H   L   T   D   Y   E   K   I   K   E   G   F>

1110        1120        1130        1140        1150
CAAGAACAAGAACGCCGATATGATCAAGTCCGCTTTCCTCCCAACCGGTG
  K   N   K   N   A   D   M   I   K   S   A   F   L   P   T   G>

1160        1170        1180        1190        1200
CATTCAAAGCAGATAGATACAAGTCTCACGGTAAGGGTTACAACTGGGGA
  A   F   K   A   D   R   Y   K   S   H   G   K   G   Y   N   W   G>

1210        1220        1230        1240        1250
AACTACAACAGAGAAACCCAAAAGTGTGAAATCTTCAACGTCAAGCCTAC
  N   Y   N   R   E   T   Q   K   C   E   I   F   N   V   K   P   T>

1260        1270        1280        1290        1300
CTGCCTCATCAACGACAAGTCCTACATTGCGACTACTGCCCTGTCTCATC
  C   L   I   N   D   K   S   Y   I   A   T   T   A   L   S   H>
```

FIG. 1B

```
          1310       1320       1330       1340       1350
CAATCGAAGTCGAACACAACTTCCCCTGCAGTCTCTACAAGGACGAGATC
  P  I  E  V  E  H  N  F  P  C  S  L  Y  K  D  E  I>

1360       1370       1380       1390       1400
AAGAAGGAAATCGAGCGTGAAAGTAAGCGTATCAAGTTGAACGATAACGA
  K  K  E  I  E  R  E  S  K  R  I  K  L  N  D  N  D>

1410       1420       1430       1440       1450
CGACGAAGGTAACAAGAAGATCATCGCACCTAGGATCTTCATCTCCGATG
   D  E  G  N  K  K  I  I  A  P  R  I  F  I  S  D>

1460       1470       1480       1490       1500
ACAAGGATTCCCTCAAGTGTCCTTGTGACCCTGAGATGGTGAGTCAGTCC
  D  K  D  S  L  K  C  P  C  D  P  E  M  V  S  Q  S>

1510       1520       1530       1540       1550
ACTTGTAGATTCTTCGTTTGCAAGTGCGTCGAACGTAGAGCCGAAGTCAC
  T  C  R  F  F  V  C  K  C  V  E  R  R  A  E  V  T>

1560       1570       1580       1590       1600
TAGTAACAACGAAGTTGTCGTGAAGGAAGAATACAAGGATGAATACGCTG
     S  N  N  E  V  V  V  K  E  E  Y  K  D  E  Y  A>

1610       1620       1630       1640       1650
ATATTCCAGAGCATAAGCCTACGTACGATAACATGAAGATCATCATCGCT
  D  I  P  E  H  K  P  T  Y  D  N  M  K  I  I  I  A>

1660       1670       1680       1690       1700
AGTTCTGCTGCTGTCGCTGTTCTGGCTACTATCCTCATGGTGTACCTTTA
  S  S  A  A  V  A  V  L  A  T  I  L  M  V  Y  L  Y>

1710       1720       1730       1740       1750
CAAGAGAAAGGGAAACGCTGAGAAGTACGACAAGATGGATCAACCTCAAC
  K  R  K  G  N  A  E  K  Y  D  K  M  D  Q  P  Q>

1760       1770       1780       1790       1800
ATTACGGTAAGAGTACTTCCAGGAACGATGAGATGTTGGATCCAGAGGCC
  H  Y  G  K  S  T  S  R  N  D  E  M  L  D  P  E  A>

1810       1820       1830       1840       1850
TCCTTCTGGGGTGAGGAGAAGAGAGCCTCTCATACTACTCCAGTTTTGAT
  S  F  W  G  E  E  K  R  A  S  H  T  T  P  V  L  M>

1860
GGAGAAGCCTTACTACTAA
  E  K  P  Y  Y  *>
```

FIG. 1C

SEQUENCE LISTING

<160> NUMBER OF SEQ ID NOS: 7

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: primer
      PF83A
<220> FEATURE:
<221> NAME/KEY: misc_feature
<222> LOCATION: (1)..(32)

<400> SEQUENCE: 1
gggggatcca tgagaaaatt atactgcgta tt                                   32

<210> SEQ ID NO 2
<211> LENGTH: 40
<212> TYPE: DNA

```
<213> ORGANISM: Artificial Sequence
<220> FEATURE:
<223> OTHER INFORMATION: Description of Artificial Sequence: primer
      PF83B
<220> FEATURE:
<221> NAME/KEY: misc_feature
<222> LOCATION: (1)..(40)

<400> SEQUENCE: 2
acgtggatcc ttaatagtat ggtttttcca tcagaactgg                              40

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: primer
      Pf83A
<220> FEATURE:
<221> NAME/KEY: misc_feature
<222> LOCATION: (1)..(27)

<400> SEQUENCE: 3
ggaattccag aactactggg agcatcc                                            27

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: primer
      Pf83H
<220> FEATURE:
<221> NAME/KEY: misc_feature
<222> LOCATION: (1)..(29)

<400> SEQUENCE: 4
gctctagaat gttatcgtaa cgtaggctt                                          29

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: primer
      Pf83I
<220> FEATURE:
<221> NAME/KEY: misc_feature
<222> LOCATION: (1)..(32)

<400> SEQUENCE: 5
gctctagact acatgttatc gtacgtaggc tt                                      32

<210> SEQ ID NO 6
<211> LENGTH: 1869
<212> TYPE: DNA
<213> ORGANISM: Artificial Sequence
<220> FEATURE:
<223> OTHER INFORMATION: Description of Combined DNA/RNA Molecule:
      synthetic gene encoding P. Falciparum AMA-1
      ectodomain with P. pastoris codon usage
<220> FEATURE:
<223> OTHER INFORMATION: Description of Artificial Sequence: synthetic
      gene encoding P. Falciparum AMA-1 ectodomain with P. pastoris
      codon usage
<220> FEATURE:
<221> NAME/KEY: CDS
<222> LOCATION: (1)..(1866)

<400> SEQUENCE: 6 atg agg aag ttg tac tgc gtt ttg ttg ttg tct gct ttc gag ttc acc          48
```

```
Met Arg Lys Leu Tyr Cys Val Leu Leu Leu Ser Ala Phe Glu Phe Thr
 1               5                  10                  15 tac atg atc aac ttc ggt cgt ggt cag aac tac tgg gag cat cct tac        96
Tyr Met Ile Asn Phe Gly Arg Gly Gln Asn Tyr Trp Glu His Pro Tyr
                 20                  25                  30 cag aag tct gac gtc tac cat cct atc aac gaa cat agg gag cat cct       144
Gln Lys Ser Asp Val Tyr His Pro Ile Asn Glu His Arg Glu His Pro
             35                  40                  45 aag gaa tac gaa tac cca ctg cat caa gag cac act tac cag cag gaa       192
Lys Glu Tyr Glu Tyr Pro Leu His Gln Glu His Thr Tyr Gln Gln Glu
         50                  55                  60 gat tct ggt gaa gat gaa aac acc ttg caa cac gct tac ccc atc gat       240
Asp Ser Gly Glu Asp Glu Asn Thr Leu Gln His Ala Tyr Pro Ile Asp
 65                  70                  75                  80 cat gaa gga gct gaa cca gcc cct cag gaa caa aac ttg ttc tct tcc       288
His Glu Gly Ala Glu Pro Ala Pro Gln Glu Gln Asn Leu Phe Ser Ser
                 85                  90                  95 atc gaa atc gtg gaa aga tcc aac tac atg ggt aac cca tgg act gag       336
Ile Glu Ile Val Glu Arg Ser Asn Tyr Met Gly Asn Pro Trp Thr Glu
            100                 105                 110 tac atg gca aag tac gac atc gag gaa gtg cac gga agt ggt atc agg       384
Tyr Met Ala Lys Tyr Asp Ile Glu Glu Val His Gly Ser Gly Ile Arg
            115                 120                 125 gtt gat ctg ggt gaa gat gcc gaa gtc gct ggt act cag tac aga ctc       432
Val Asp Leu Gly Glu Asp Ala Glu Val Ala Gly Thr Gln Tyr Arg Leu
        130                 135                 140 cct tct ggt aag tgc cct gtt ttc gga aag ggt atc atc atc gaa aac       480
Pro Ser Gly Lys Cys Pro Val Phe Gly Lys Gly Ile Ile Ile Glu Asn
145                 150                 155                 160 tct aag act act ttc ctc aag cct gtt gct act ggt aac caa gat ctt       528
Ser Lys Thr Thr Phe Leu Lys Pro Val Ala Thr Gly Asn Gln Asp Leu
                165                 170                 175 aag gac gga ggt ttc gct ttc cca cct act aac cct ctg atc tct cca       576
Lys Asp Gly Gly Phe Ala Phe Pro Pro Thr Asn Pro Leu Ile Ser Pro
            180                 185                 190 atg act ttg aac ggt atg cgt gac ttc tac aag aac aac gaa tac gtc       624
Met Thr Leu Asn Gly Met Arg Asp Phe Tyr Lys Asn Asn Glu Tyr Val
            195                 200                 205 aag aac ttg gat gaa ttg act ttg tgt agt aga cac gct gga aac atg       672
Lys Asn Leu Asp Glu Leu Thr Leu Cys Ser Arg His Ala Gly Asn Met
        210                 215                 220 aac cct gat aac gac aag aac agt aac tac aag tac ccc gcg gtt tac       720
Asn Pro Asp Asn Asp Lys Asn Ser Asn Tyr Lys Tyr Pro Ala Val Tyr
225                 230                 235                 240 gac tac aac gat aag aag tgt cac atc ctg tac atc gct gcc caa gaa       768
Asp Tyr Asn Asp Lys Lys Cys His Ile Leu Tyr Ile Ala Ala Gln Glu
                245                 250                 255 aac aac gga cca aga tac tgt aac aag gat caa agt aag aga aac tct       816
Asn Asn Gly Pro Arg Tyr Cys Asn Lys Asp Gln Ser Lys Arg Asn Ser
            260                 265                 270 atg ttc tgt ttc aga cct gca aag gac aag ctg ttc gaa aac tac gtg       864
Met Phe Cys Phe Arg Pro Ala Lys Asp Lys Leu Phe Glu Asn Tyr Val
            275                 280                 285 tac ttg tcc aag aac gtt gtc gat aac tgg gaa gaa gtc tgc cca aga       912
Tyr Leu Ser Lys Asn Val Val Asp Asn Trp Glu Glu Val Cys Pro Arg
        290                 295                 300 aag aac ctc gag aac gca aag ttc ggt ctg tgg gtc gat ggt aac tgt       960
Lys Asn Leu Glu Asn Ala Lys Phe Gly Leu Trp Val Asp Gly Asn Cys
305                 310                 315                 320 gaa gac atc cct cat gtg aac gag ttc agt gct aac gat ttg ttc gag      1008
```

```
                Glu Asp Ile Pro His Val Asn Glu Phe Ser Ala Asn Asp Leu Phe Glu
                                325                 330                 335 tgt aac aag ctg gtc ttc gag ttg tct gcc agt gac caa cct aag cag        1056
Cys Asn Lys Leu Val Phe Glu Leu Ser Ala Ser Asp Gln Pro Lys Gln
                340                 345                 350 tac gaa cag cat ttg act gac tac gaa aag atc aag gaa gga ttc aag        1104
Tyr Glu Gln His Leu Thr Asp Tyr Glu Lys Ile Lys Glu Gly Phe Lys
            355                 360                 365 aac aag aac gcc gat atg atc aag tcc gct ttc ctc cca acc ggt gca        1152
Asn Lys Asn Ala Asp Met Ile Lys Ser Ala Phe Leu Pro Thr Gly Ala
        370                 375                 380 ttc aaa gca gat aga tac aag tct cac ggt aag ggt tac aac tgg gga        1200
Phe Lys Ala Asp Arg Tyr Lys Ser His Gly Lys Gly Tyr Asn Trp Gly
385                 390                 395                 400 aac tac aac aga gaa acc caa aag tgt gaa atc ttc aac gtc aag cct        1248
Asn Tyr Asn Arg Glu Thr Gln Lys Cys Glu Ile Phe Asn Val Lys Pro
                405                 410                 415 acc tgc ctc atc aac gac aag tcc tac att gcg act act gcc ctg tct        1296
Thr Cys Leu Ile Asn Asp Lys Ser Tyr Ile Ala Thr Thr Ala Leu Ser
            420                 425                 430 cat cca atc gaa gtc gaa cac aac ttc ccc tgc agt ctc tac aag gac        1344
His Pro Ile Glu Val Glu His Asn Phe Pro Cys Ser Leu Tyr Lys Asp
        435                 440                 445 gag atc aag aag gaa atc gag cgt gaa agt aag cgt atc aag ttg aac        1392
Glu Ile Lys Lys Glu Ile Glu Arg Glu Ser Lys Arg Ile Lys Leu Asn
    450                 455                 460 gat aac gac gac gaa ggt aac aag aag atc atc gca cct agg atc ttc        1440
Asp Asn Asp Asp Glu Gly Asn Lys Lys Ile Ile Ala Pro Arg Ile Phe
465                 470                 475                 480 atc tcc gat gac aag gat tcc ctc aag tgt cct tgt gac cct gag atg        1488
Ile Ser Asp Asp Lys Asp Ser Leu Lys Cys Pro Cys Asp Pro Glu Met
                485                 490                 495 gtg agt cag tcc act tgt aga ttc ttc gtt tgc aag tgc gtc gaa cgt        1536
Val Ser Gln Ser Thr Cys Arg Phe Phe Val Cys Lys Cys Val Glu Arg
            500                 505                 510 aga gcc gaa gtc act agt aac aac gaa gtt gtc gtg aag gaa gaa tac        1584
Arg Ala Glu Val Thr Ser Asn Asn Glu Val Val Val Lys Glu Glu Tyr
        515                 520                 525 aag gat gaa tac gct gat att cca gag cat aag cct acg tac gat aac        1632
Lys Asp Glu Tyr Ala Asp Ile Pro Glu His Lys Pro Thr Tyr Asp Asn
    530                 535                 540 atg aag atc atc atc gct agt tct gct gct gtc gct gtt ctg gct act        1680
Met Lys Ile Ile Ile Ala Ser Ser Ala Ala Val Ala Val Leu Ala Thr
545                 550                 555                 560 atc ctc atg gtg tac ctt tac aag aga aag gga aac gct gag aag tac        1728
Ile Leu Met Val Tyr Leu Tyr Lys Arg Lys Gly Asn Ala Glu Lys Tyr
                565                 570                 575 gac aag atg gat caa cct caa cat tac ggt aag agt act tcc agg aac        1776
Asp Lys Met Asp Gln Pro Gln His Tyr Gly Lys Ser Thr Ser Arg Asn
            580                 585                 590 gat gag atg ttg gat cca gag gcc tcc ttc tgg ggt gag gag aag aga        1824
Asp Glu Met Leu Asp Pro Glu Ala Ser Phe Trp Gly Glu Glu Lys Arg
        595                 600                 605 gcc tct cat act act cca gtt ttg atg gag aag cct tac tac taa            1869
Ala Ser His Thr Thr Pro Val Leu Met Glu Lys Pro Tyr Tyr
    610                 615                 620

<210> SEQ ID NO 7
<211> LENGTH: 622
<212> TYPE: PRT
<213> ORGANISM: Artificial Sequence
```

<220> FEATURE:
<223> OTHER INFORMATION: Description of Artificial Sequence: synthetic gene encoding P. Falciparum AMA-1 ectodomain with P. pastoris codon usage

<400> SEQUENCE: 7

```
Met Arg Lys Leu Tyr Cys Val Leu Leu Ser Ala Phe Glu Phe Thr
 1               5                  10                  15

Tyr Met Ile Asn Phe Gly Arg Gly Gln Asn Tyr Trp Glu His Pro Tyr
             20                  25                  30

Gln Lys Ser Asp Val Tyr His Pro Ile Asn Glu His Arg Glu His Pro
         35                  40                  45

Lys Glu Tyr Glu Tyr Pro Leu His Gln Glu His Thr Tyr Gln Gln Glu
     50                  55                  60

Asp Ser Gly Glu Asp Glu Asn Thr Leu Gln His Ala Tyr Pro Ile Asp
 65                  70                  75                  80

His Glu Gly Ala Glu Pro Ala Pro Gln Glu Gln Asn Leu Phe Ser Ser
                 85                  90                  95

Ile Glu Ile Val Glu Arg Ser Asn Tyr Met Gly Asn Pro Trp Thr Glu
            100                 105                 110

Tyr Met Ala Lys Tyr Asp Ile Glu Glu Val His Gly Ser Gly Ile Arg
            115                 120                 125

Val Asp Leu Gly Glu Asp Ala Glu Val Ala Gly Thr Gln Tyr Arg Leu
        130                 135                 140

Pro Ser Gly Lys Cys Pro Val Phe Gly Lys Gly Ile Ile Ile Glu Asn
145                 150                 155                 160

Ser Lys Thr Thr Phe Leu Lys Pro Val Ala Thr Gly Asn Gln Asp Leu
                165                 170                 175

Lys Asp Gly Gly Phe Ala Phe Pro Pro Thr Asn Pro Leu Ile Ser Pro
            180                 185                 190

Met Thr Leu Asn Gly Met Arg Asp Phe Tyr Lys Asn Asn Glu Tyr Val
            195                 200                 205

Lys Asn Leu Asp Glu Leu Thr Leu Cys Ser Arg His Ala Gly Asn Met
        210                 215                 220

Asn Pro Asp Asn Asp Lys Asn Ser Asn Tyr Lys Tyr Pro Ala Val Tyr
225                 230                 235                 240

Asp Tyr Asn Asp Lys Lys Cys His Ile Leu Tyr Ile Ala Ala Gln Glu
                245                 250                 255

Asn Asn Gly Pro Arg Tyr Cys Asn Lys Asp Gln Ser Lys Arg Asn Ser
            260                 265                 270

Met Phe Cys Phe Arg Pro Ala Lys Asp Lys Leu Phe Glu Asn Tyr Val
            275                 280                 285

Tyr Leu Ser Lys Asn Val Val Asp Asn Trp Glu Val Cys Pro Arg
        290                 295                 300

Lys Asn Leu Glu Asn Ala Lys Phe Gly Leu Trp Val Asp Gly Asn Cys
305                 310                 315                 320

Glu Asp Ile Pro His Val Asn Glu Phe Ser Ala Asn Asp Leu Phe Glu
                325                 330                 335

Cys Asn Lys Leu Val Phe Glu Leu Ser Ala Ser Asp Gln Pro Lys Gln
            340                 345                 350

Tyr Glu Gln His Leu Thr Asp Tyr Glu Lys Ile Lys Glu Gly Phe Lys
        355                 360                 365

Asn Lys Asn Ala Asp Met Ile Lys Ser Ala Phe Leu Pro Thr Gly Ala
    370                 375                 380

Phe Lys Ala Asp Arg Tyr Lys Ser His Gly Lys Gly Tyr Asn Trp Gly
```

-continued

```
            385              390              395              400
Asn Tyr Asn Arg Glu Thr Gln Lys Cys Glu Ile Phe Asn Val Lys Pro
                405              410              415

Thr Cys Leu Ile Asn Asp Lys Ser Tyr Ile Ala Thr Thr Ala Leu Ser
                420              425              430

His Pro Ile Glu Val Glu His Asn Phe Pro Cys Ser Leu Tyr Lys Asp
            435              440              445

Glu Ile Lys Lys Glu Ile Glu Arg Glu Ser Lys Arg Ile Lys Leu Asn
        450              455              460

Asp Asn Asp Asp Glu Gly Asn Lys Lys Ile Ile Ala Pro Arg Ile Phe
465              470              475              480

Ile Ser Asp Asp Lys Asp Ser Leu Lys Cys Pro Cys Asp Pro Glu Met
                485              490              495

Val Ser Gln Ser Thr Cys Arg Phe Phe Val Cys Lys Cys Val Glu Arg
                500              505              510

Arg Ala Glu Val Thr Ser Asn Asn Glu Val Val Val Lys Glu Glu Tyr
            515              520              525

Lys Asp Glu Tyr Ala Asp Ile Pro Glu His Lys Pro Thr Tyr Asp Asn
        530              535              540

Met Lys Ile Ile Ile Ala Ser Ser Ala Ala Val Ala Val Leu Ala Thr
545              550              555              560

Ile Leu Met Val Tyr Leu Tyr Lys Arg Lys Gly Asn Ala Glu Lys Tyr
                565              570              575

Asp Lys Met Asp Gln Pro Gln His Tyr Gly Lys Ser Thr Ser Arg Asn
                580              585              590

Asp Glu Met Leu Asp Pro Glu Ala Ser Phe Trp Gly Glu Glu Lys Arg
            595              600              605

Ala Ser His Thr Thr Pro Val Leu Met Glu Lys Pro Tyr Tyr
            610              615              620
```

EFFICIENT EXPRESSION OF *PLASMODIUM* APICAL MEMBRANE ANTIGEN IN YEAST CELLS

CROSS-REFERENCE TO RELATED APPLICATION

This application is a continuation of PCT International Patent Application No. PCT/NL/01/00934, filed on Dec. 21, 2001, designating the United States of America, and published, in English, as PCT International Publication No. WO 02/052014 A2 on Jul. 4, 2002, the contents of the entirety of which is incorporated herein by this reference.

TECHNICAL FIELD

The invention relates to the fields of medicine and biotechnology, vaccines and diagnostics. More in particular, the invention relates to the intervention and the diagnosis of *Plasmodium*-induced malaria.

BACKGROUND

Malaria is a widespread disease in most subtropical countries. It is acquired by infection with a malaria parasite. The socioeconomic impact of this disease is enormous. Malaria exists in different forms, caused by different parasites. The symptoms vary considerably between the different forms.

*Plasmodium vivax* and *Plasmodium falciparum* are the two most important human malaria parasites. Other human malaria parasites are *Plasmodium ovale* and *Plasmodium malariae*, but these two species are less pathogenic than *P. vivax* and *P. falciparum*. *P. vivax* causes less mortality than *P. falciparum*. Treatment of *P. falciparum* is becoming more complicated, because chloroquine-resistant *P. falciparum* parasites are spreading rapidly and multidrug-resistant parasites have also developed. In addition, chloroquine-resistant *P. vivax* has been detected, indicating similar problems in the treatment of *P. vivax* as for *P. falciparum*.

At present, there is essentially no effective vaccine available against malaria, at least not for use in humans. Accumulated data, including that from nonhuman primate[1,2] and rodent studies,[3,4] have indicated that the apical membrane antigen-1 (AMA-1) family of molecules is a target for protective immune responses. In all *Plasmodium* species reported to date, with the exception of *P. falciparum*[5] and *P. reichenowi*[6] that form a phylogenetic Glade distinct from other malaria parasites, AMA-1 is synthesized de novo as a 66 kDa transmembrane protein. The protein contains a predicted N-terminal signal sequence, an ectodomain, a predicted transmembrane region and a C-terminal cytoplasmic domain. The ectodomain is further divided into three domains (domain I, II and III) defined by disulfide bonds.[7] In *P. falciparum* and *P. reichenowi*, the protein is expressed as an 83 kDa protein having an N-terminal extension as compared to the 66 kDa forms, referred to as the prosequence. Intraspecies sequence polymorphism due to point mutations[8,9,10] reveals clustering of mutations in particular domains of the molecule. Despite this, between species there is considerable conservation of primary amino acid structure and predicted secondary structure. Evidence to date indicates that protection invoked by AMA-1 is directed at conformational epitopes[1, 3, 4, 11] located in the AMA-1 ectodomain. Immunization with reduced AMA-1 fails to induce parasite inhibitory antibodies,[3, 11] and so far only those monoclonal antibodies that recognize reduction-sensitive conformational AMA-1 epitopes have been shown to inhibit parasite multiplication in vitro for *P. knowlesi*[12, 13] and *P. falciparum*.[6, 14] This indicates that for an AMA-1 vaccine, the correct conformation will be critical.

Recombinant expression of *P. falciparum* AMA-1 (Pf AMA-1) in a conformationally relevant way that allows production of clinical grade material has been notoriously difficult. One characteristic important for recombinant expression techniques is the unusually high A+T content of *P. falciparum* codons in comparison to most other organisms and, in particular, in comparison to most other organisms generally used for recombinant protein expression. The group of Prof. Anders (WEHI, Australia) has developed expression of the ectodomain in *E. coli*, followed by a refolding protocol, but scaling up this process to levels that allow production of clinical grade material has proven cumbersome. Because eukaryotic expression systems are likely to produce material with the correct disulphide bonds directly, we have focused upon expression in such systems. Expression of the full-length 622 amino acids long Pf AMA-1 protein (7G8 strain) in insect cells using recombinant baculovirus resulted in expression on the surface of insect cells.[15] The protein migrated in SDS-PAGE more slowly than the native molecule, indicating glycosylation. Expression in the presence of tunicamycin confirmed this. The Pf AMA-1 protein was used to raise rat monoclonal antibodies (mAbs), some of which could block parasite multiplication in an in vitro assay. These functional mAbs recognized a conformational epitope located in the ectodomain of Pf AMA-1. Reactivity with these mAbs, especially with mAb 4G2, is used as one assay for proper folding of recombinant Pf AMA-1. Relatively low expression levels did not allow the baculovirus system to be developed for the production of clinical grade material.

We have obtained high-level expression of *P. vivax* AMA-1 (Pv AMA-1) ectodomain in the methylotrophic yeast *Pichia pastoris*.[16] However, this expression system is not likewise suitable to produce a secreted ectodomain of Pf AMA-1. Using the same expression vector as has successfully been used for Pv AMA-1, recombinant Pf AMA-1 *P. pastoris* clones do not express Pf AMA-1 ectodomain at any level. Analysis of total RNA extracted from induced cultures revealed only truncated mRNA products for Pf AMA-1, so no effective expression of Pf AMA-1 was possible until the present invention. This was a problem because expression of homogeneous Pf AMA-1 in high amounts is highly desirable. Efficient production of Pf AMA-1 gives possibilities to develop a diagnostics or a vaccine and/or a medicine against *P. falciparum* and/or other *Plasmodium* species. Presently, such a vaccine or medicine is not available.

BRIEF SUMMARY OF THE INVENTION

The present invention provides a method for producing mRNA encoding the *Plasmodium* AMA-1 ectodomain, or a functional part, derivative, and/or analogue thereof, in a yeast cell, comprising providing the yeast cell with a nucleic acid encoding the *Plasmodium* AMA-1 ectodomain or a functional part, derivative, and/or analogue thereof, the nucleic acid being modified to utilize the yeast cell's codon usage. Preferably, the ectodomain is derived from an 83 kDa AMA-1 protein. Particularly, the ectodomains of 83 kDa AMA-1 proteins are difficult to express in yeast cells. More preferably, the 83 kDa AMA-1 protein is derived from *P. falciparum*. Now that a method of the invention is available, it is also possible to produce an analogous protein, such as a complete AMA-1 protein. Thus, the invention also provides a method for producing mRNA encoding *Plasmodium* AMA-1 protein, or a functional part, derivative, and/or analogue thereof, in a yeast cell, comprising providing the yeast cell with a nucleic acid encoding the *Plasmodium* AMA-1 protein, the nucleic acid being modified to utilize the yeast cell's codon usage. AMA-1 ectodomain produced with a method of the invention comprises at least one conformational epitope that is comparable to a conformational epitope in the native AMA-1 ectodomain, produced by the parasite, preferably in a human host. The AMA-1 ectodomain of the invention can be used for vaccination purposes and for diagnostic purposes.

With a method of the invention, it is possible to obtain mRNA encoding the AMA-1 ectodomain in a yeast cell. In the yeast cell, mRNA is efficiently translated into a functional AMA-1 ectodomain. With the teachings of the invention, a person skilled in the art is able to produce a functional part, derivative, and/or analogue of the ectodomain comprising at least one immunogenic property of native ectodomain in kind, not necessarily in amount.

In a preferred embodiment, a method of the invention further comprises allowing for expression of the *Plasmodium* AMA-1 ectodomain or functional part, derivative, and/or analogue thereof, in the yeast cell. Preferably, the AMA-1 ectodomain or functional part, derivative, and/or analogue thereof, is purified from the yeast cell and/or culture medium.

By a "*Plasmodium* AMA-1 ectodomain" is meant herein a part of a *Plasmodium* AMA-1 protein which is normally present between the N-terminal signal sequence and the transmembrane region of a naturally occurring *Plasmodium* AMA-1 protein. In *P. falciparum*, the ectodomain normally spans amino acid residues 25 to 545 of SEQ ID NO:7. In a preferred embodiment, an ectodomain of the invention spans an amino acid sequence corresponding to amino acid residues 25 to 545 of SEQ ID NO:7 in *P. falciparum*.

A functional part of a *Plasmodium* AMA-1 ectodomain is defined herein as a part which comprises at least one immunogenic property of the AMA-1 ectodomain in kind, not necessarily in amount. Preferably, the functional part comprises at least part of the prosequence, domain I, domain II and/or domain III of a *P. falciparum* AMA-1 ectodomain. More preferably, the functional part spans an amino acid sequence corresponding to amino acid residues 25-442, 97-318, 97-442, 97-545, 303-442, 303-544, and/or 419-544 of SEQ ID NO:7 in *P. falciparum*.

In one embodiment, the functional part comprises a subdomain of ectodomain, which can be defined, for instance, by disulphide bond patterning: By "immunogenic property" is meant the capability to induce an immune response in a host. Preferably, immunogenic property comprises a property to induce an immune response against a conformational epitope on a native AMA-1 ectodomain. A functional derivative of a *Plasmodium* AMA-1 ectodomain is defined as a *Plasmodium* AMA-1 ectodomain which has been altered such that at least one immunogenic property of the molecule is essentially the same in kind, not necessarily in amount. A derivative can be provided in many ways, for instance, through conservative amino acid substitution. A derivative can also be a fusion of the AMA-1 ectodomain or a part thereof with a second protein. In a preferred embodiment, the derivative comprises one or more amino acids from variant AMA-1 ectodomains. The resultant AMA-1 ectodomain is a consensus AMA-1 ectodomain having no naturally occurring counterpart. A person skilled in the art is well able to generate analogous compounds of a *Plasmodium* AMA-1 ectodomain. This can, for instance, be done through screening of a peptide library. Such an analogue comprises at least one immunogenic property of a *Plasmodium* AMA-1 ectodomain in kind, not necessarily in amount. For the present invention, complete AMA-1 protein and shorter versions comprising a complete ectodomain are analogous to ectodomain.

Compared to the reported Pf AMA-1 genes, the A+T(U) content of a nucleic acid of the invention is reduced without changing amino acid sequences (with the exception of glycosylation sites, as described below). Preferably, the A+T(U) content is reduced in a putative yeast polyadenylation consensus sequence to prevent premature termination of transcription. Such sequences are highly A+T rich and are thus more likely to be present within the A+T rich coding sequences of *P. falciparum* genes. Thus, one embodiment of the invention discloses a method of the invention, wherein at least one putative yeast polyadenylation consensus sequence in the nucleic acid has been modified.

Another problem for expression in eukaryotic systems is N-glycosylation. *P. falciparum* blood stage proteins are not N-glycosylated by the parasite. However, Pf AMA-1 contains six N-glycosylation sites that are potentially recognized by other eukaryotic systems. Full-length 7G8 Pf AMA-1 expressed in insect cells is glycosylated. Expression of Pv AMA-1 ectodomain in *Pichia* showed heterogeneous glycosylation of the recombinant product.[16] This could only partly be prevented by the addition of extremely high levels of tunicamycin to induction cultures, at the cost of a large drop in expression levels. Deglycosylation using N-glycosidase F was only complete after full denaturation of the protein, a process which would need refolding protocols to obtain properly folded material. Therefore, a preferred embodiment of the invention discloses a method of the invention, wherein at least one site in the *Plasmodium* AMA-1 ectodomain or functional part, derivative, and/or analogue thereof, that is generally glycosylated by eukaryotic expression systems is removed. These sites may generally be glycosylated by eukaryotic expression systems through the N-glycosylation pathway. The site may be removed by mutating the nucleic acid sequence encoding the site. This may lead to a change of at least one amino acid composing the site. This change may decrease the eukaryotic system's capability of glycosylating the site. Alternatively, amino acids which are part of the site may be removed without substitution. This may be accomplished by removing a part of the nucleic acid encoding the site. In the present invention, it has been found that at least one *Plasmodium* AMA-1 ectodomain potential glycosylation site can be altered to prevent glycosylation at the site in a eukaryotic host, while the altered *Plasmodium* AMA-1 ectodomain retains a capability of raising a cross-reaction immune response in an animal against an unmodified *Plasmodium* AMA-1 protein.

The reasoning for removing a glycosylation site is threefold. First, the presence and location of N-linked glycosylation can have profound but unpredictable targeting and focusing effects on the immune response to proteins.[17] In this context, the Pf AMA-1 baculovirus product had been used in protection studies in Aotus monkeys. These unpublished studies did not show a protective effect of AMA-1 immunization. Although one explanation for this may have been that a suboptimal adjuvant was used to formulate the antigen, we reasoned that the glycosylation of the Pf AMA-1 may also have significantly influenced the immune response in an unbeneficial way. Second, glycosylation is frequently heterogeneous (as demonstrated by expression of the native sequence Pv AMA-1 ectodomain in *Pichia*). Heterogeneous products may be difficult to reproducibly purify to acceptable standards under GMP, and such heterogeneity may create batch-to-batch variation in an immunogenic property of the product (given the published effects of N-linked glycosylation on immunogenicity). Third, we wished to produce a protein with the least heterogeneity in order to prepare crystals for crystallographic determination of structure. It is generally accepted that the more homogeneous the protein, the higher the chances of successful crystal formation.

Based on the molecular weight of expressed AMA-1 protein in various *Plasmodium* species, two groups of *Plasmodium* species can be identified. Those expressing an AMA-1 protein of approximately 66 kDa and those expressing an AMA-1 protein of approximately 83 kDa. A method of the invention is particularly suited to increase levels of expression of ectodomain of the approximately 83 kDa AMA-1 protein in yeast. Measuring the exact molecular weight of a protein is always a difficult task; thus, for the present invention, the number of 83 kDa should be taken as a guidance for the actual molecular weight of the AMA-1 protein. Variations of 10% in the estimates for molecular weight of a given protein are not abnormal. However, considering the large difference between the two variants of AMA-1 (66 versus 83 kDa), the size indication is only required to help a person skilled in the art determine whether the AMA-1 protein at hand belongs to one or the other class. A variation in the molecular weight measurements of 10% can easily be tolerated while still being able to select one of the two classes of AMA-1 proteins. Thus, in a preferred embodiment of the invention, the *Plasmodium* belongs to the Glade whose members normally express the AMA-1 protein as an approximately 83 kDa protein. "Normally" is herein defined as under conditions occurring in nature. As has already been described in this disclosure, *P. falciparum* and *P. reichenowi* belong to the Glade which has the characteristic of expressing the AMA-1 protein as an 83 kDa protein. Another preferred embodiment of the invention discloses a method, wherein the *Plasmodium* comprises *P. falciparum*. Preferably, the *Plasmodium* comprises *P. falciparum* FVO. We have developed the PfAMA-1 sequence from the FVO strain of *P. falciparum* for expression in *P. pastoris* for several reasons. The challenge strain that is likely to be used in phase II clinical trials is the 3D7 clone of NF54. The FVO strain has an AMA-1 sequence that is one of the most divergent from 3D7 reported to date, and, therefore, immunization with FVO AMA-1 would allow for a markedly heterologous challenge. Because of the possibility that polymorphism in AMA-1 is selected and maintained because of immune pressure, the availability of two extremes of diversity for clinical testing apart and in combination will be extremely informative. In addition, the FVO strain has been adapted to grow in *Aotus lemurinus griseimembra* monkeys, thus allowing preclinical evaluation with homologous challenge possibilities in this nonhuman primate system. FVO as well as 3D7 strains react with mAb 4G2, showing epitope conservation between the divergent AMA-1 sequences.

Another preferred embodiment of the invention discloses a method according to the invention, wherein the yeast is *Pichia*. Yet another preferred embodiment of the invention discloses a method according to the invention, wherein the yeast is *Pichia pastoris*.

In another aspect, the present invention discloses an isolated and/or recombinant nucleic acid sequence encoding the *Plasmodium* AMA-1 ectodomain or a functional part, derivative, and/or analogue thereof, the nucleic acid being modified to utilize a yeast cell's codon usage. A functional part, derivative, and/or analogue of an AMA-1 ectodomain comprises at least one conformational epitope of the native AMA-1 ectodomain; preferably, the conformational epitope is an ectodomain epitope. Preferably, the nucleic acid encodes a *P. falciparum* AMA-1 ectodomain, more preferably, a *P. falciparum* FVO AMA-1 ectodomain.

As has been described above, preferably at least one putative yeast polyadenylation consensus sequence has been modified in a nucleic acid of the invention. Also, preferably at least one site in the *Plasmodium* AMA-1 ectodomain, or functional part, derivative, and/or analogue thereof, that is generally glycosylated by eukaryotic expression systems is removed. Thus, in a preferred aspect, the invention discloses an isolated and/or recombinant nucleic acid sequence according to the invention, wherein at least one putative yeast polyadenylation consensus sequence has been modified. In another preferred aspect, the invention discloses an isolated and/or recombinant nucleic acid sequence according to the invention wherein at least one site in the ectodomain or functional part, derivative, and/or analogue thereof, that is generally glycosylated by eukaryotic expression systems is removed.

FIG. 1 shows a nucleic acid of the invention, comprising the above-mentioned preferred characteristics. Thus, in one aspect, the present invention discloses an isolated and/or recombinant nucleic acid sequence encoding the *Plasmodium* AMA-1 ectodomain (SEQ ID NO:7) or a functional part, derivative, and/or analogue thereof, the nucleic acid comprising a sequence as depicted in FIG. 1 (SEQ ID NO:6).

Considering that in the present invention a nucleic acid sequence was generated that was modified to utilize a yeast cell's codon usage and that can be used to express high amounts of *Plasmodium* AMA-1 ectodomain in a yeast cell, and the fact that AMA-1 amino acid sequences of various species comprise significant homology, the present invention further provides a nucleic acid sequence encoding *Plasmodium* AMA-1 ectodomain or a functional part, derivative, and/or analogue thereof, capable of hybridizing to at least a functional part of a nucleic acid of the invention. In a preferred embodiment, the invention provides a nucleic acid sequence encoding *P. falciparum* AMA-1 ectodomain or a functional part, derivative, and/or analogue thereof, capable of hybridizing to at least a functional part of a nucleic acid of the invention. Through the hybridization criterion, it is warranted that the nucleic acid sequence comprises similar expression characteristics (in kind, not necessarily in amount) in yeast cells, at least on an mRNA level as the nucleic acid of FIG. 1 which utilizes a yeast cell's codon usage. By "at least a functional part of a nucleic acid of the invention" is meant a part of the nucleic acid, at least 30 base pairs long, preferably at least 200 base pairs long, comprising at least one expression characteristic (in kind, not necessarily in amount) as a nucleic acid of the invention. Preferably, but not necessarily, the part comprises an immunogenic property of an AMA-1 ectodomain. In one aspect of the invention, hybridizing to at least a functional part of a nucleic acid of the invention is under stringent conditions.

In another aspect, the invention provides an AMA-1-specific nucleic acid sequence comprising at least 50 percent homology to a nucleic acid sequence of the invention. An "AMA-1-specific nucleic acid sequence" is defined herein as a nucleic acid sequence, comprising at least 20 nucleotides, preferably at least 50 nucleotides, the sequence comprising a nucleic acid sequence corresponding to at least part of an AMA-1 gene, or comprising a nucleic acid sequence which is complementary to a sequence corresponding to at least part of an AMA-1 gene. In a preferred aspect of the present invention, the AMA-1-specific nucleic acid sequence comprises at least 60 percent homology to a nucleic acid of the invention. More preferably, the AMA-1-specific nucleic acid sequence comprises at least 75 percent homology to a nucleic acid of the invention. In a most preferred aspect of the invention, the AMA-1-specific nucleic acid sequence comprises at least 90 percent homology to a nucleic acid of the invention. Preferably, the homology is calculated using the *Plasmodium* AMA-1 ectodomain-specific sequence as depicted in FIG. 1 as a reference.

With the teachings of the present invention, a person skilled in the art is capable of generating a nucleic acid sequence comprising an immunogenic property of an AMA-1 ectodomain from another species of *Plasmodium*, for instance, *P. vivax*, while still using essentially the same nucleic acid sequence as given in FIG. 1. Such variant nucleic acid will, of course, still be able to hybridize to at least a functional part of the nucleic acid depicted in FIG. 1.

In a preferred embodiment, the present invention discloses a nucleic acid sequence according to the invention, wherein the *Plasmodium* belongs to the Glade whose members express the AMA-1 protein as an approximately 83 kDa protein. As has been described before, *P. falciparum* and *P. reichenowi* belong to this Glade. More preferably, the *Plasmodium* comprises *P. falciparum*. More preferably, *Plasmodium* comprises *P. falciparum* FVO.

A nucleic acid of the invention may, for instance, encode a derivative of a *Plasmodium* AMA-1 ectodomain or part thereof, comprising one or more amino acids from variant AMA-1 ectodomains. The resultant AMA-1 ectodomain or part thereof is a consensus AMA-1 ectodomain having no naturally occurring counterpart. Thus, in one aspect, the invention provides a nucleic acid sequence according to the invention, wherein the *Plasmodium* AMA-1 ectodomain or functional part, derivative, and/or analogue thereof, comprises a consensus *Plasmodium* AMA-1 ectodomain or functional part, derivative, and/or analogue thereof. In a preferred embodiment, part of an AMA-1 ectodomain comprises at least one immunogenic property of the ectodomain. In another aspect, a nucleic acid of the invention may be modified to utilize codon usage of *Pichia*. Thus, in one aspect, the invention provides a nucleic acid sequence according to the invention, wherein the yeast is *Pichia*. Preferably, the yeast is *Pichia pastoris*.

A nucleic acid of the invention is particularly suitable for efficient expression of the *Plasmodium* AMA-1 ectodomain or a functional part, derivative, and/or analogue thereof. Therefore, in another aspect, the present invention provides a method for producing the *Plasmodium* AMA-1 ectodomain or a functional part, derivative, and/or analogue thereof, comprising:

providing a yeast cell with a nucleic acid according to the invention, and collecting the formed *Plasmodium* AMA-1 ectodomain or functional part, derivative, and/or analogue thereof.

Preferably, the yeast is *Pichia* yeast, more preferably, *P. pastoris*. Alternatively, it is possible to express a nucleic acid of the invention in another eukaryotic system, for instance, baculovirus or a CHO cell. It is even possible to express a nucleic acid of the invention in bacteria. Eukaryotic systems and bacteria are more capable of expressing a nucleic acid utilizing the yeast cell's codon usage, compared to a nucleic acid utilizing *P. falciparum*'s codon usage. However, a nucleic acid of the invention can also be modified to utilize codon usage of other eukaryotic systems or bacteria. Preferably, the nucleic acid has been modified to remove at least one putative polyadenylation consensus sequence which is recognized by the other eukaryotic system. More preferably, at least one site in the nucleic acid that is generally glycosylated by the other eukaryotic expression system is removed. Expression of a nucleic acid of the invention in another eukaryotic system or bacteria, as mentioned above, is still within the scope of the present invention.

Of course, by using a method as previously described, *Plasmodium* AMA-1 ectodomain or a functional part, derivative, and/or analogue will be produced. Thus, another aspect of the invention provides a *Plasmodium* AMA-1 ectodomain or a functional part, derivative, and/or analogue thereof, obtainable by a method of the invention. The invention further provides a Pf AMA-1 ectodomain or functional part, derivative, and/or analogue thereof, produced in a yeast cell. In a preferred embodiment, the AMA-1 ectodomain or functional part, derivative, and/or analogue thereof, is purified. As is described in example 4.3, with a method of the invention, it is possible to obtain the desired Pf AMA-1 ectodomain, without contaminants, such as a 50 kDa contaminant. Thus, in a preferred aspect, the invention provides a method further comprising purifying the *Plasmodium* AMA-1 ectodomain or functional part, derivative, and/or analogue thereof.

A cell producing the *Plasmodium* AMA-1 ectodomain, or a functional part, derivative, and/or analogue thereof, by a method as previously described is, of course, also within the scope of the present invention. Yet another aspect of the invention provides an isolated cell comprising a nucleic acid of the invention.

In yet another aspect, the invention provides an isolated cell comprising a *Plasmodium* AMA-1 ectodomain of the invention or functional part, derivative, and/or analogue thereof.

*Plasmodium* AMA-1 is particularly well suited for the preparation of a vaccine, because accumulated data have indicated that this family of molecules is a target for protective immune responses. As the present invention provides a way of producing a *Plasmodium* AMA-1 ectodomain or a functional part, derivative, and/or analogue thereof, efficiently, the invention also provides use of a *Plasmodium* AMA-1 ectodomain or functional part, derivative, and/or analogue thereof, according to the invention for the preparation of a vaccine. A vaccine comprises a *Plasmodium* AMA-1 ectodomain or functional part, derivative, and/or analogue thereof, according to the invention, and a suitable expedient is, of course, also herewith provided. Preferably, the vaccine comprises a suitable adjuvant.

In a preferred embodiment, at least two different variants of *Plasmodium* AMA-1 ectodomains or functional parts, derivatives and/or analogues thereof according to the invention are used for the preparation of a vaccine. Immunization with different variants of a *Plasmodium* ectodomain or functional part, derivative, and/or analogue thereof, provides a broader protection. The vaccine preferably comprises *Plasmodium* AMA-1 ectodomains or functional parts, derivatives and/or analogues thereof from different *Plasmodium* parasites from the same Glade. More preferably, the vaccine comprises *Plasmodium* AMA-1 ectodomains or functional parts, derivatives and/or analogues thereof from different *Plasmodium* parasites from the same species. Most preferably, the species comprises *P. falciparum*. A vaccine of the invention preferably comprises *Plasmodium* AMA-1 ectodomains or functional parts, derivatives and/or analogues thereof which display mutual differences, because then a broad protection is even better acquired. An analysis performed by us of *P. falciparum* variants has revealed that these variants display mutual differences of between 1 and about 30 amino acid residues. Therefore, a vaccine of the invention preferably comprises *Plasmodium* AMA-1 ectodomains or functional parts, derivatives and/or analogues thereof displaying mutual differences of 1-35, more preferably 15-35, most preferably 25-35 amino acid residues. The vaccine may, for instance, comprise *P. falciparum* FVO Pf83 and *P. falciparum* 3D7 AMA-1 ectodomains or functional parts, derivatives and/or analogues thereof.

Different variants of a *Plasmodium* ectodomain or functional part, derivative, and/or analogue thereof, according to the invention can, for instance, be administered together to an individual at the same time. Alternatively, immunization can be performed with one variant, followed by boosting with another variant. This way, protection against common epitopes is boosted and the formation of parasite invasion inhibitory antibodies which are reactive with a whole range of *Plasmodium* strains is enhanced.

In a preferred embodiment, a vaccine of the invention comprises a *Plasmodium* AMA-1 ectodomain or functional part, derivative, and/or analogue thereof, linked to C3d. Preferably, C3d is covalently linked. C3d is a complement component that cross-links receptors on B-cells, thus activating them. This results in enhanced antibody production.

In another preferred embodiment, the invention provides a vaccine comprising a combination of a *Plasmodium* AMA-1 ectodomain or functional part, derivative, and/or analogue thereof, and another *Plasmodium* immunogenic protein or functional part, derivative, and/or analogue thereof, for instance, *Plasmodium* MSP-1. This way, an even broader protection can be acquired. The proteins can be present in the vaccine as separate proteins. Alternatively, the proteins can be linked together or be part of a fusion protein. MSP-1, like AMA-1, is involved in the invasion of red blood cells by merozoites. MSP-1 is expressed on the surface of merozoites. Antibodies directed towards the C-terminal end of MSP-1 and reactive with conformational epitopes are capable of blocking invasion in vitro.

In yet another aspect, the invention provides use of a proteinaceous molecule capable of binding a *Plasmodium* AMA-1 ectodomain or a functional part, derivative, and/or analogue thereof, for the preparation of a vaccine. The proteinaceous molecule, for instance, comprises an antibody raised against Pf AMA-1. After administration of the proteinaceous molecule to an individual, the individual is, at least temporarily, protected. The antibody is preferably a human or humanized antibody. It may be generated in vitro using recombinant antibody technology. Alternatively, it may be isolated from blood or serum obtained from an individual vaccinated by a vaccine of the invention. A vaccine comprising a proteinaceous molecule capable of binding a *Plasmodium* AMA-1 ectodomain or a functional part, derivative, and/or analogue thereof, and a suitable expedient is, therefore, also herewith provided. Preferably, a vaccine of the invention is provided wherein the *Plasmodium* comprises *P. falciparum*. More preferably, the *Plasmodium* comprises *P. falciparum* FVO.

Of course, a vaccine of the invention is particularly well suited for the prophylaxis of malaria. Thus, the invention provides use of a *Plasmodium* AMA-1 ectodomain or functional part, derivative, and/or analogue thereof, according to the invention for the preparation of a vaccine for prevention of malaria.

In a particular embodiment, the invention provides a use of a *Plasmodium* AMA-1 ectodomain or functional part, derivative, and/or analogue thereof, according to the invention for the preparation of a vaccine for prevention of malaria, wherein malaria is caused by *P. falciparum*. A proteinaceous molecule capable of binding a *Plasmodium* AMA-1 ectodomain or a functional part, derivative, and/or analogue thereof, is also well suited for the preparation of a medicament. Preferably, the proteinaceous molecule is used for the preparation of a medicament against malaria.

A *Plasmodium* AMA-1 ectodomain according to the invention is also well suited for diagnosis of malaria. A person skilled in the art can think of many ways of determining the presence of *Plasmodium* AMA-1 ectodomain, or antibodies against *Plasmodium* AMA-1 ectodomain, in a patient. One way is, for instance, collecting a blood sample of a patient. The blood sample can be administered to a well which contains *Plasmodium* AMA-1 ectodomain of the invention. If the patient contains antibodies against *Plasmodium* AMA-1 ectodomain, the antibodies will bind to the *Plasmodium* AMA-1 ectodomain in the well. These antibodies can be made visible by many techniques known in the art, for instance, by incubation with fluorescent-labeled rabbit anti-human antibodies. Many other ways are known in the art which are still within the scope of the present invention. Thus, the present invention provides a use of a *Plasmodium* AMA-1 ectodomain or functional part, derivative, and/or analogue thereof, according to the invention for diagnosis of malaria.

Another embodiment provides a method for, at least in part, diagnosis of malaria, comprising collecting a sample from an individual and providing *Plasmodium* AMA-1 ectodomain or functional part, derivative, and/or analogue thereof, of the invention with at least part of the sample. Preferably, the sample is a blood sample.

Another embodiment of the present invention provides a method for, at least in part, prophylaxis of malaria, comprising administering a vaccine according to the invention to an individual. Yet another embodiment provides a method for, at least in part, prophylaxis of malaria, comprising administering a proteinaceous molecule capable of binding a *Plasmodium* AMA-1 ectodomain or a functional part, derivative, and/or analogue thereof, to an individual. However, an immune response is often only high directly after administration of a vaccine to an individual. Likewise, protection acquired by administered proteinaceous molecules capable of binding a *Plasmodium* AMA-1 ectodomain or a functional part, derivative, and/or analogue thereof, is often only high directly after administration of the proteinaceous molecules to an individual. Therefore, a preferred embodiment of the present invention provides a method for, at least in part, prophylaxis of malaria comprising administering to an individual slow release compositions comprising a vaccine of the invention.

By "slow release composition" is meant a composition from which a vaccine of the invention is only slowly migrated into the body. This way, the body contains a vaccine of the invention for a prolonged period, so the immune response will be high during a prolonged period of time.

BRIEF DESCRIPTION OF THE DRAWING

FIG. 1 is a sequence of an isolated and/or recombinant nucleic acid (SEQ ID NO:6) of the present invention, encoding *Plasmodium* AMA-1 ectodomain (SEQ ID NO:7). Surprisingly, this sequence is very well expressed in *Pichia pastoris*, whereas a nucleic acid sequence encoding wild-type Pf AMA-1 ectodomain is not.

DETAILED DESCRIPTION OF THE INVENTION

The following examples illustrate the present invention. The examples do not limit the present invention in any way. A

EXAMPLES

Example 1

Development of Synthetic Gene for *P. falciparum* FVO Strain Pf AMA-1

1.1 Original FVO Sequence

Cryopreserved parasite stocks from *P. falciparum* FVO were prepared from an infected *Aotus lemurinus griseimembra* monkey at the young ring stage of development and DNA was isolated (Gentra Systems Inc., Minneapolis, Minn.) directly from a parasite stock according to the manufacturer's instructions. Pf AMA-1 was amplified by polymerase chain reaction using Pfu polymerase (Promega, Leiden, The Netherlands) and primers PF83A: 5'-GGGGGATCCAT-GAGAAAATTATACTGCGTATT-3' (nt 1-23 and additional BamHI restriction site, SEQ ID NO:1) and PF83B: 5'-ACGTGGATCCTTAATAGTATGGTTTTTC-CATCAGAACTGG-3' (complementary to nt 1843-1869 and additional BamHI restriction site, SEQ ID NO:2) containing BamHI restriction sites to facilitate cloning in pBluescript. A pool of four independent clones was used for sequence analysis using an ABI PRISM™ 310 automated sequencer (PE Applied Biosystems, Foster City, Calif.) according to the manufacturer's instructions, and primers previously synthesized for sequencing of Pf AMA-1.1[10] This resulted in the unambiguous sequence of *P. falciparum* FVO Pf AMA-1, that differs from the FVO AMA-1 sequence available from Genbank (accession number U84348) at three amino acid positions. The most notable difference is that the Genbank FVO AMA-1 sequence is one amino acid shorter than any other available AMA-1 sequence, and our FVO AMA-1 sequence does not have this deletion.

1.2 Alteration of N-Glycosylation Sites

The sequence of gene Pf AMA-1 from the FVO strain that we have established, encodes a protein of 622 amino acid residues that has six potential N-glycosylation sites. Our previous experience with expressing Pf AMA-1 in baculovirus/insect cells as well as with expressing Pv AMA-1 in *P. pastoris* has shown that these N-glycosylation sites will be glycosylated in eukaryotic heterologous expression systems. As explained above, this is undesirable since native Pf AMA-1 is not glycosylated. Therefore, we developed a variant that exploited the lack of conservation of N-glycosylation sites in published *Plasmodium* AMA-1 allele sequences. Asn 162 was changed to Lys that is present in that position in the Thai-Tn strain Pf AMA-1 (accession number M58547). Thr 288 was changed to Val (present in *P. vivax* and *P. knowlesi* AMA-1; accession numbers Y16950 and M61097); Ser 373 was changed to Asp (present in *P. knowlesi* AMA-1); Asn 422 and Ser 423 were changed to Asp and Lys, respectively (present in *P. knowlesi*, *P. vivax*, *P. chabaudi* (accession number M25248) and *P. fragile* AMA-1 (accession number M29898)) and Asn 499 was changed to Gln (present in *P. chabaudi* AMA-1).

1.3 Synthetic Gene with *P. pastoris* Codon Usage

The nucleotide sequence with the six changed codons to delete the potential N-glycosylation sites was used to develop a synthetic gene utilizing the codon usage of *P. pastoris* (NIMR, London). Our previous experience with expressing Pf AMA-1 in *P. pastoris* taught us that the high A+T content of the *P. falciparum* gene makes it extremely difficult to express this in *P. pastoris*. There are several A+T rich regions within the coding sequence that are recognized as transcription termination and/or polyadenylation sites in yeast, resulting in truncated mRNAs and no protein production. The sequence of the synthetic gene was designed according to *P. pastoris* codon usage with the aid of the CODOP program.[18] This program allows codon optimization with host organism preference. It enabled design of an optimal sequence, with strategic insertion of restriction sites, and the generation of oligos of 40 nucleotides in length from both strands of the gene. The resulting set of 92 oligos was rigorously screened for the presence of potential transcription termination signals and undesirable repeats, inverted repeats, and regions of complementarity which could potentially lead to nonspecific intermolecular hybridization. The 20 nucleotide overlap between each 40-mer primer was adjusted to give a melting temperature in the range of 62-68° C., in order to allow subsequent use of the primers for DNA sequencing. Gene synthesis was by assembly polymerase chain reaction (PCR), using the proof-reading Pfu DNA polymerase, as described in reference.[18] Blunt-ended PCR products corresponding to each "half" of the gene were cloned into pMosBlue (Amersham Pharmacia) and fully sequenced on both strands before subcloning to produce the complete synthetic gene. The final product was again sequenced on both strands. The sequence of the synthetic gene FVO Pf83syn is provided in FIG. 1.

Example 2

Expression of FVO Pf83syn Ectodomain in *P. pastoris*

2.1 Development of Expression Constructs

For secreted expression in *P. pastoris* strain KM71H, we used vector pPICZα A (Invitrogen). This vector provides an N-terminal signal sequence and a C-terminal myc epitope followed by a 6×His tag for easy purification. Gene fragments have to be cloned in frame with these sequences. Primers for PCR amplification of the Pf AMA-1 ectodomain were Pf83A: 5'-GGAATTCCAGAACTACTGGGAGCATCC-3' (nt 73-92 and additional EcoRI restriction site, SEQ ID NO:3) and Pf83H: 5'-GCTCTAGAATGTTATCGTAACGTAGGCTT-3' (complementary to nt 1615-1634 and additional XbaI restriction site, SEQ ID NO:4) or Pf83A and Pf83I: 5'-GCTCTA-GACTACATGTTATCGTACGTAGGCTT-3' (complementary to nt 1615-1635, plus stop codon plus additional XbaI restriction site; this provides the full ectodomain without myc epitope and His tag, SEQ ID NO:5). A 50 µL PCR reaction contained 10 ng template DNA (FVO Pf83syn), 100 ng of each of the primers Pf83A and Pf83H, or Pf83A and Pf83I, 0.2 mM dNTP, 5 µL 10×Pfu reaction buffer and 1 unit Pfu polymerase (Promega). Amplification proceeded as follows: 1 minute, 94° C., 1 minute 52° C., 1.5 minutes 72° C. for 3 cycles; 1 minute, 94° C., 1 minute 60° C., 1.5 minutes 72° C. for 30 cycles; 5 minute, 72° C. and then stored at 4° C. The resulting 1578 bp PCR product was digested with EcoRI and XbaI sequentially, and ligated into EcoRI/XbaI digested pPICZα A in a 1:10 molar ratio. *E. coli* DH5α subcloning efficiency cells were transformed with 5 µL of the ligation mixture and plated on low salt LB plates containing 25 µg/ml zeocin and cultured overnight at 37° C. Colonies were grown in low salt LB containing 25 µg/ml zeocin, plasmids were isolated by standard miniprep methods and analyzed by restriction enzyme digestion. One clone containing the correct insertion for each of the PCR products (named Pf4 mH for primers A and H, and Pf11-0 for primers A and I) was used to isolate plasmid DNA for transformation of *P. pastoris*.

2.2 *Pichia* Transformation and Analysis

The expression construct was linearized with SstI and 10 μg DNA was used to transform 80 μL *P. pastoris* KM71H cells by electroporation following the Invitrogen protocols. 1 ml of 1M sorbitol was added and the cells were allowed to recover for two hours at 30° C. Cells were then plated (25, 50, 100, 200 μL aliquots) on YPDS (1% yeast extract, 2% peptone, 2% dextrose, 1 M sorbitol) agar plates containing 100 μg/ml zeocin, and incubated for 4 days at 30° C. Colonies were picked and grown for 2 days at 30° C. in 10 ml of BMGY (1% yeast extract, 2% peptone, 1.34% Yeast Nitrogen Base, 1% glycerol, 0.4 mg/L biotin, 0.1M K-phosphate pH 6.0) in 50 ml Falcon tubes with vigorous shaking. Cells were harvested by low-speed centrifugation, resuspended in 4 ml of BMMY (BMGY with glycerol substituted for 0.5% methanol), and cultured for an additional 2 days. Cells were harvested and the culture supernatants were analyzed for the presence of PfAMA-1 ectodomain by SDS-PAGE. Gels were stained with Coomassie Brilliant Blue. All clones analyzed expressed an equal amount of two proteins in the culture supernatant. A 50 kDa molecule of thus far unknown origin, as well as an approximately 75 kDa protein, which proved to be the Pf AMA-1 ectodomain, with or without myc epitope and His tag (Pf4 mH and Pf11-0, respectively). Expression levels in these small scale cultures are estimated to be 50 mg/L. Our experience with the expression of Pv AMA-1 in *P. pastoris* suggests that this might result in levels approaching 1 g/L in optimized fermentations. No obvious degradation products were visible in the culture supernatants.

Culture supernatants of Pf4 mH were spot blotted on nitrocellulose membranes and incubated with rat monoclonal antibody 58F8 (recognizing a linear epitope in the N-terminal region of Pf AMA-1), or 4G2 recognizing a conformational epitope in the ectodomain and capable of blocking parasite multiplication in vitro) for one hour at room temperature. After incubation with goat-anti-rat IgG, color was developed using NBT/BCIP. Only culture supernatants from the recombinant *P. pastoris* expressing the 75 kDa protein reacted with both mAbs. Control culture supernatants, where the 50 kDa protein, but not the 75 kDa protein, was present did not react with either of the mAbs. This indicates that the 75 kDa protein is the PfAMA-1 ectodomain and that the secreted material is properly folded. As expected, reactivity with 4G2 was lost when the culture supernatant was reduced with β-mercaptoethanol prior to spot blotting, demonstrating the correct disulfide bond formation within the ectodomain to recreate the 4G2 epitope.

Purified Pf4 mH (sec 4) was used in a standard ELISA to test reactivity with mAb 4G2 and a human serum from an African endemic region. These human sera show high reactivity with conformational epitopes of AMA-1, and hardly react with reduced AMA-1. In this ELISA, strong reactivity with 4G2 and the human serum was detected, whereas a control mAb and a pool of European human serum did not react. As a positive control, similar amounts of baculovirus-produced Pf AMA-1 were coated on an ELISA plate and incubated with the same serum samples. Similar results were obtained, although reactivity was much lower, suggesting a much better quality for the *Pichia* Pf4 mH product.

In addition, rabbit sera raised against the baculovirus-produced PfAMA-1 displayed much lower titers on Pf4 mH than rabbit sera raised against Pf4 mH. This was not due to impurities in the Pf4 mH preparation, since: 1) a very low reactivity of the anti-Pf4 mH sera against *Pichia* proteins was observed, and 2) anti-Pichia antisera were only marginally reactive with contaminations in purified Pf4 mH by Western blotting. These results indicate that the baculovirus-produced Pf AMA-1 is less immunogenic, most likely due to the relative impurity of the purified product and/or heterogeneity in folding of the product.

The homogeneity of the *Pichia*-produced Pf4 mH was further evaluated by immuno-affinity chromatography, using immobilized mAb 4G2, reactive with a conformational epitope. It was found that Pf4 mH quantitatively bound to the immobilized mAb, demonstrating that every molecule has the proper conformation.

To determine a Pf AMA-1 epitope for mAb 4G2, we expressed separate domains of Pf AMA-1 and combinations thereof using the same *P. pastoris* system as for Pf4 mH. These are:

Pf3 mH: amino acid residues 25-442 (prosequence, domains I and II);
Pf8 mH: amino acid residues 303-442 (domain II);
Pf9 mH: amino acid residues 303-544 (domains II and III);
Pf10mH: residues 419-544 (domain III); and
Pf14-0: residues 97-545 (domains I, II, III). Residue 97 is the natural N-terminus of the 66 kDa proteolytic product of the 83 kDa Pf AMA-1.21 We established that the parasite-inhibitory mAb 4G2 is only reactive with Pf3 mH, Pf4 mH and Pf14-0, and not with any of the other proteins. This maps an epitope for 4G2 to domain I or domains I+II.

Immunogenicity has been evaluated in rabbits by four immunizations of 100 microgram protein formulated in Freunds complete (1st injection) or Freunds incomplete (remaining injections) adjuvant. Injections were given at days 0, 14, 28 and 56, and antisera obtained four weeks after the final boost were tested by ELISA and immunofluorescence (IFA). Results for Pf4 mH are summarized in Table 1 and IFA data from the other rabbit sera are summarized in Table 2. It is clear that all AMA-1 domains produced by us are capable of inducing high levels of antibodies that are reactive with the native parasite protein. Using the same protocol, the immunogenicity of two additional fragments are evaluated. These fragments comprise:

1) amino acid residues 97-442 (domain I+II), and
2) amino acid residues 97-318 (domain I).

IgG was purified from immunized rabbits using standard procedures, and the capacity to inhibit *P. falciparum* growth in vitro was evaluated. Parasites at mature schizont stage were cultured in 96-well plates in the presence of different concentrations of IgG from the immunized rabbits, or of IgG from control rabbits immunized with adjuvant only, or purified mAb 4G2 IgG. Radiolabel was added after reinvasion of erythrocytes had occurred (approximately 17 hours later) and in vitro culture was continued for another ten hours. Parasites were harvested onto glass fiber filters using a Titertek cell harvester (ICN). Incorporation of [$^3$H]hypoxanthine was determined by liquid scintillation spectrometry. Parasite growth inhibition, reported as a percentage, was determined as follows: 100−((average $CPM_{experimental}$/average $CPM$ $control_{control}$)×100). The incorporation of erythrocytes alone was subtracted from all averages prior to determining the percentage inhibition. Control IgG was isolated from rabbits that had been immunized with adjuvant only.

In this assay, mAb 4G2 at 1 mg/ml gives 50-60% inhibition of invasion, irrespective of the *P. falciparum* strain used. Data for the Pf4 mH-immunized rabbit IgGs are given in Table 1. We used FCR3 as the homologous strain, since AMA-1 differs by only 1 amino acid residue, located in the pro-sequence, from FVO AMA-1. NF54 was used as the heterologous strain and differs by 29 amino acids from FVO AMA-1. Total IgG from rabbits immunized with Pf4 mH inhibit invasion of the homologous strain up to 85% at 1.5 mg/ml (a concentration far below standard serum IgG concentrations), and of the heterologous strain up to 58%. This indicates the presence of common, as well as strain-specific, epitopes and demonstrates the capacity of the *Pichia*-produced Pf AMA-1 ectodomain to induce potent parasite-inhibitory antibodies.

TABLE 1

Analysis of anti-Pf4mH responses

| Rabbit | ELISA titer | | IFA titer | | Inhibition of invasion[1] | |
|---|---|---|---|---|---|---|
| | Pf4mH | pPICZα | FCR3 | NF54 | FCR3 | NF54 |
| 1 | $2.5 \times 10^6$ | $4 \times 10^4$ | $2.5 \times 10^5$ | $1.3 \times 10^5$ | 85% | 55% |
| 2 | $2.5 \times 10^6$ | $4 \times 10^4$ | $2.5 \times 10^5$ | $0.6 \times 10^5$ | 75% | 58% |
| 3 | $1.3 \times 10^6$ | $<1 \times 10^4$ | $1.3 \times 10^5$ | $0.3 \times 10^5$ | 50% | 44% |

[1]evaluated using purified IgG at 1.5 mg · ml$^{-1}$

TABLE 2

Immunogenicity of AMA-1 domains

| Rabbit ID | Antigen | AMA-1 residues | IFA titer FCR3 |
|---|---|---|---|
| 715 | Pf11-0 | 25-545 | $2.5 \times 10^5$ |
| 716 | | | $5.1 \times 10^5$ |
| 717 | | | $2.5 \times 10^5$ |
| 709 | Pf3mH | 25-442 | $2.5 \times 10^5$ |
| 710 | | | $2.5 \times 10^5$ |
| 771 | Pf8mH | 303-442 | $1.3 \times 10^5$ |
| 772 | | | $2.5 \times 10^5$ |
| 773 | Pf9mH | 303-544 | $1.3 \times 10^5$ |
| 774 | | | $1.3 \times 10^5$ |
| 775 | Pf10mH | 419-544 | $0.3 \times 10^5$ |
| 776 | | | $1.3 \times 10^5$ |

Example 3

Bulk Production

Pf11-0.1 has undergone a feasibility study for GMP production at a GMP production facility. Pilot fermentations at 5-10 L scale have been performed to assess parameters that influence proteolytic degradation and yield. The conclusion was that addition of 0.4 mM EDTA to the standard fermentation medium at pH 6.0, as well as methanol induction with a high cell density for a short period of 30 hours, and immediate freezing of the harvested culture supernatant until processing, are all beneficial to prevent proteolytic degradation. For purification, best results were obtained by direct binding of Pf AMA-1 on an immobilized metal affinity column activated with CuSO$_4$ (LMAC). This step also removes proteases from Pf AMA-1 resulting in an increase in stability of the partially purified product. The general conclusion of the feasibility study is that it is feasible to produce 1 gram of protein with a minimum purity of 98% for Phase I clinical testing.

For mid-scale production of Pf AMA-1 ectodomain, recombinant *P. pastoris* was cultured in 1 L baffled flasks (400 ml BMGY per flask) for 48 hours at 29-30° C. under vigorous shaking. Cells were harvested and resuspended in 100 ml BMMY, and then cultured for 48 hours at 29-30° C. under vigorous shaking. Methanol was added to a final concentration of 0.5% every 24 hours. After low-speed centrifugation, the culture supernatant was harvested. Protein was precipitated with ammonium sulphate (70% final concentration) at 0° C., and the precipitate was stored at 4° C. until use.

Example 4

Purification Strategies 4.1 Purification of Pf4mH on Ni Resins

Additional proof that the secreted 75 kDa protein is the Pf AMA-1 ectodomain comes from purification using Ni resins, since recombinant proteins produced using the pPICZα vector contain His tags that have a high affinity for Ni. The ammonium sulphate precipitate of 50 ml culture supernatant was solubilized in 2 ml binding buffer (20 mM Na Phosphate pH 7.8, 0.5 M NaCl) and loaded on an 8 ml Ni-agarose column (Probond, Bio-Rad) at 0.2 ml/minute. The column was washed at 1 ml/minute with 15 ml binding buffer, 25 ml of the same buffer pH 6.0, 15 ml of the buffer pH 5.5 and then eluted with the same buffer at pH 4.0. Elution was monitored at 280 nm. The pH 4.0 peak fractions contained a single protein of 75 kDa as determined by SDS-PAGE analysis. Alternatively, the 75 kDa ectodomain could be eluted with a linear 0-500 mM Imidazole gradient in 20 mM Na Phosphate pH 6.0, 0.5 M NaCl. Spot blotting of the peak fractions revealed strong 4G2 and 58F8 binding, indicating that the 75 kDa protein is the His-tagged Pf AMA-1 ectodomain. The 50 kDa protein present in the culture supernatant as well as yellow-stained flavin components were present in the flow through and pH 6.0 wash fractions.

4.2 Other Purification Strategies for Pf11-0

Other purification strategies are needed when the ectodomain is expressed without His tag, which might be more appropriate for clinical purposes. One way of purifying the 75 kDa ectodomain Pf11-0 away from the 50 kDa protein is the use of hydroxy apatite (HAP)[19,20] chromatography.

The ammonium sulphate precipitate of a 100 ml culture supernatant was solubilized in 5 ml 10 mM NaPO$_4$, pH 6.8 and loaded onto a prepacked 5 ml HAP column (CHT-II, Bio-Rad) at 0.5 ml/minute. Elution with a 20 ml gradient to 400 mM NaPO$_4$, pH 6.8 at 1 ml/minute was monitored at 280 nm. Two overlapping peaks were evident, the first one containing mainly the 50 kDa protein, the second one mainly the Pf AMA-1 ectodomain. Further purification could be obtained by subsequent anion exchange chromatography of the pooled second peak fractions after diluting 1:10 in miliQ water on a prepacked 5 ml UNO Q column (Bio-Rad), eluted with a linear gradient of 0-0.5 M NaCl in 20 mM Tris HCl pH 7.6. This results in several peaks containing the remainder of the 50 kDa contaminant as well as several degradation products of the AMA-1 ectodomain, and a single peak that contains pure intact AMA-1 ectodomain, as analyzed by reduced SDS-PAGE and Coomassie staining.

4.3 Production of Pf11-0 without the Contaminating 50 kDa Protein

The 50 kDa protein present in the culture supernatant of our recombinant *P. pastoris* KM71H clones is not common (information from Invitrogen). Transformation of just the empty pPICZα vector into the same batch of *P. pastoris* KM71H also yielded a 50 kDa protein in the culture supernatant upon methanol induction. Untransformed *P. pastoris* KM71H does not produce this protein. We have now succeeded in preparing a new clone (Pf11-0.1) that only secretes the 75 kDa Pf AMA-1 ectodomain upon methanol induction, and that does not produce the 50 kDa contaminant. This was achieved by picking a single colony of *P. pastoris* KM71H from a freshly prepared agar plate, made from the original stock of that strain. This colony was used to start fresh cultures that were transformed with the Pf11-0 vector, resulting in the above-described expression.

Purification as described under 4.2 will provide higher yields of pure Pf AMA-1 ectodomain, since there is no need to separate the 75 kDa product from a major contaminant any more, thus allowing recovery of the complete peak fraction 20 from the HAP column for further anion exchange chromatography purification.

REFERENCES

1. Collins, W. E., et al., Protective immunity induced in squirrel monkeys with recombinant apical membrane antigen-1 of *Plasmodium fragile*. *Am. J. Trop. Med. Hyg.*, 1994. 51(6): p. 711-9.
2. Deans, J. A. and W. C. Jean, Structural studies on a putative protective *Plasmodium knowlesi* merozoite antigen. *Mol. Biochem. Parasitol.*, 1987. 26(1-2): p. 155-66.
3. Anders, R. F., et al., Immunisation with recombinant AMA-1 protects mice against infection with *Plasmodium chabaudi*. *Vaccine*, 1998. 16(2-3): p. 240-7.
4. Crewther, P. E., et al., Protective immune responses to apical membrane antigen 1 of *Plasmodium chabaudi* involve recognition of strain-specific epitopes. *Infect. Immun.*, 1996. 64(8): p. 3310-7.
5. Peterson, M. G., et al., Integral membrane protein located in the apical complex of *Plasmodium falciparum*. *Mol. Cell. Biol.*, 1989. 9(7): p. 3151-4.
6. Kocken, C. H., et al., Molecular characterisation of *Plasmodium reichenowi* apical membrane antigen-1 (AMA-1), comparison with *P. falciparum* AMA-1, and antibody-mediated inhibition of red cell invasion [In Process Citation]. *Mol. Biochem. Parasitol.*, 2000. 109(2): p. 147-56.
7. Hodder, A. N., et al., The disulfide bond structure of *Plasmodium* apical membrane antigen-1. *J. Biol. Chem.*, 1996. 271(46): p. 29446-52.
8. Marshall, V. M., et al., Diversity of the vaccine candidate AMA-1 of *Plasmodium falciparum*. *Mol. Biochem. Parasitol.*, 1996. 77(1): p. 109-13.
9. Oliveira, D. A., et al., Genetic conservation of the *Plasmodium falciparum* apical membrane antigen-1 (AMA-1). *Mol. Biochem. Parasitol.*, 1996. 76(1-2): p. 333-6.
10. Thomas, A. W., A. P. Waters, and D. Can, Analysis of variation in PF83, an erythrocytic merozoite vaccine candidate antigen of *Plasmodium falciparum*. *Mol. Biochem. Parasitol.*, 1990. 42(2): p. 285-7.
11. Deans, J. A., et al., Vaccination trials in rhesus monkeys with a minor, invariant, *Plasmodium knowlesi* 66 kD merozoite antigen. *Parasite Immunol.*, 1988. 10(5): p. 535-52.
12. Deans, J. A., et al., Rat monoclonal antibodies which inhibit the in vitro multiplication of *Plasmodium knowlesi*. *Clin. Exp. Immunol.*, 1982. 49(2): p. 297-309.
13. Thomas, A. W., et al., The Fab fragments of monoclonal IgG to a merozoite surface antigen inhibit *Plasmodium knowlesi* invasion of erythrocytes. *Mol. Biochem. Parasitol.*, 1984. 13(2): p. 187-99.
14. Kocken, C. H., et al., Precise timing of expression of a *Plasmodium falciparum*-derived transgene in *Plasmodium berghei* is a critical determinant of subsequent subcellular localization. *J. Biol. Chem.*, 1998. 273(24): p. 15119-24.
15. Narum, D. L., G. W. Welling, and A. W. Thomas, Ion-exchange-immunoaffinity purification of a recombinant baculovirus *Plasmodium falciparum* apical membrane antigen, PF83/AMA-1. *J. Chromatogr. A.*, 1993. 657(2): p. 357-63.
16. Kocken, C. H., et al., High-level expression of *Plasmodium vivax* apical membrane antigen 1 (AMA-1) in *Pichia pastoris*: strong immunogenicity in Macaca mullatta immunized with *P. vivax* AMA-1 and adjuvant SBAS2. *Infect. Immun.*, 1999. 67(1): p. 43-9.
17. Garrity, R. R., et al., Refocusing neutralizing antibody response by targeted dampening of an immunodominant epitope. *J. Immunol.*, 1997. 159(1): p. 279-89.
18. Withers-Martinez, C., E. P. Carpenter, F. Hackett, B. Ely, M. Sajid, M. Grainger and M. J. Blackman. PCR-based gene synthesis as an efficient approach for expression of the A+T-rich malaria genome. *Prot. Engineering* 12, 1999. 1113-1120.
19. Urist, M. R., et al., Purification of bovine bone morphogenetic protein by hydroxyapatite chromatography. *Proc. Natl. Acad. Sci. U.S.A.*, 1984. 81(2): p. 371-5.
20. Roelcke, D. and H. Jungfer, Subfractionation of gammaG-myeloma globulins by hydroxyl-apatite column chromatography. *Ger. Med. Mon.*, 1971. 1(1): p. 7-8.
21. Howell, S. A., C. Withers-Martinez, C. H. Kocken, A. W. Thomas, and M. J. Blackman (2001). Proteolytic processing and primary structure of *Plasmodium falciparum* apical membrane antigen-1 (Pf AMA-1). *J. Biol. Chem.* 276: p. 31311-20.

What is claimed is:

1. A method for producing mRNA that produces a *Plasmodium falciparum* apical membrane antigen-1 (AMA-1) ectodomain or a fragment thereof when translated in a yeast cell, said method comprising:
    providing said yeast cell with a nucleic acid encoding said ectodomain or said fragment thereof, wherein said ectodomain comprises amino acid sequence 25-545 of SEQ ID NO:7, and wherein the fragment thereof comprises an amino acid sequence selected from the group consisting of 25-442, 97-442, and 97-545 of SEQ ID NO:7, and wherein said nucleic acid encoding said ectodomain or fragment thereof has been modified to utilize said yeast cell's codon usage, and wherein mAb 4G2 exhibits specificity for said ectodomain or said fragment thereof when said ectodomain or said fragment thereof is produced in a yeast cell; and
    expressing said nucleic acid in said yeast cell, thus producing the mRNA encoding the ectodomain or the fragment thereof,
    wherein the nucleic acid encoding said fragment encodes a peptide consisting of an amino acid sequence selected from the group of amino acid sequences consisting of amino acids 25-442, 97-442, and 97-545 of SEQ ID NO: 7.

2. The method according to claim 1, further comprising translating the thus produced mRNA encoding the ectodomain or fragment thereof into a *P. falciparum* AMA-1 ectodomain peptide or a fragment peptide thereof in said yeast cell; and
    purifying said peptide or said fragment peptide thereof.

3. The method according to claim 1, wherein the mRNA encoding *Plasmodium falciparum* AMA-1 ectodomain, or fragment thereof, comprises mRNA encoding *Plasmodium falciparum* Vietnam-Oak Knoll strain ectodomain.

4. The method according to claim 1, wherein said yeast cell is *Pichia*.

5. The method according to claim 4, wherein said yeast cell is *Pichia pastoris*.

6. A process for producing a *Plasmodium falciparum* apical membrane antigen-1 (AMA-1) ectodomain or a fragment thereof, said method comprising:
    providing a yeast cell with an isolated or recombinant nucleic acid encoding said ectodomain or said fragment thereof, wherein said ectodomain comprises amino acid sequence 25-545 of SEQ ID NO:7, and wherein the fragment thereof comprises an amino acid sequence selected from the group consisting of 25-442, 97-442, and 97-545 of SEQ ID NO:7, and wherein said nucleic acid has been modified to utilize a yeast cell's codon usage, and wherein mAb 4G2 exhibits specificity for said ectodomain or said fragment thereof;
    expressing said nucleic acid, thus producing mRNA encoding said ectodomain or said fragment thereof; and
    translating the thus produced mRNA encoding the ectodomain or fragment thereof into a *P. falciparum*

AMA-1 ectodomain peptide or a fragment peptide thereof in said yeast cell, wherein the fragment peptide thereof consists of an amino acid sequence selected from the group of amino acid sequences consisting of amino acids 25-442, 97-442, and 97-545 of SEQ ID NO: 7, and collecting said ectodomain or said fragment peptide thereof.

7. The process of claim 6, further comprising purifying said ectodomain or said fragment thereof.

8. The process of claim 6, wherein said yeast cell is *Pichia*.

9. The process of claim 8, wherein said yeast cell is *Pichia pastoris*.

10. A method for producing mRNA that produces a fragment of a *Plasmodium falciparum* apical membrane antigen-1 (AMA-1) ectodomain when translated in a yeast cell, said method comprising:

providing said yeast cell with a nucleic acid encoding said fragment, wherein the fragment thereof comprises an amino acid sequence selected from the group consisting of 25-442, 97-442, and 97-545 of SEQ ID NO:7, and wherein said nucleic acid has been modified to utilize said yeast cell's codon usage, and wherein mAb 4G2 exhibits specificity for said fragment when said fragment is produced in a yeast cell; and expressing the nucleic acid in the yeast cell, thus producing the mRNA encoding the fragment, wherein the nucleic acid encoding said fragment encodes a peptide comprising an amino acid sequence selected from the group of amino acid sequences consisting of amino acids 25-442, 97-442, and 97-545 of SEQ ID NO: 7.

11. A method for producing a fragment of a *Plasmodium falciparum* apical membrane antigen-1 (AMA-1) ectodomain, said method comprising:

providing a yeast cell with an isolated or recombinant nucleic acid encoding the fragment, wherein the fragment comprises an amino acid sequence selected from the group consisting of 25-442, 97-442, and 97-545 of SEQ ID NO: 7, and wherein said nucleic acid has been modified to utilize said yeast cell's codon usage, and wherein mAb 4G2 exhibits specificity for said fragment;

expressing the nucleic acid, thus producing the mRNA encoding said fragment translating said mRNA encoding said fragment into a fragment peptide; and collecting the fragment peptide, wherein the fragment peptide consists of an amino acid sequence selected from the group of amino acid sequences consisting of amino acids 25-442, 97-442, and 97-545 of SEQ ID NO: 7.

12. A method for producing mRNA that produces a *Plasmodium falciparum* apical membrane antigen-1 (AMA-1) ectodomain or a fragment thereof when translated in a yeast cell, the method comprising:

providing the yeast cell with a nucleic acid encoding the ectodomain or the fragment thereof, wherein the ectodomain consists of amino acid sequence 25-545 of SEQ ID NO:7, and wherein the fragment thereof consists of an amino acid sequence selected from the group consisting of 25-442, 97-442, and 97-545 of SEQ ID NO:7, and wherein the nucleic acid has been modified to utilize said yeast cell's codon usage, and wherein mAb 4G2 exhibits specificity for the ectodomain or the fragment thereof when the ectodomain or the fragment thereof is produced in a yeast cell; and expressing the nucleic acid, thus producing the mRNA encoding a *Plasmodium falciparum* AMA-1 ectodomain or the fragment thereof;

wherein the nucleic acid encoding, said fragment encodes a peptide consisting of an amino acid sequence selected from the group of amino acid sequences consisting of amino acids 25-442, 97-442, and 97-545 of SEQ ID NO: 7.

13. A method for producing mRNA that produces a *Plasmodium falciparum* apical membrane antigen-1 (AMA-1) ectodomain fragment when translated in a yeast cell, said method comprising:

providing the yeast cell with a nucleic acid encoding the ectodomain fragment comprising the amino acid sequence 97-442 of SEQ ID NO:7, and wherein the nucleic acid encoding the ectodomain fragment has been modified to utilize the yeast cell's codon usage, and wherein mAb 4G2 exhibits specificity for the ectodomain fragment when the ectodomain fragment is produced in a yeast cell; and expressing the nucleic acid in the yeast cell, thus producing the mRNA encoding the ectodomain fragment, wherein the nucleic acid encoding said fragment encodes a peptide consisting of an amino acid sequence selected from the group of amino acid sequences consisting of amino acids 97-442, of SEQ ID NO: 7.

* * * * *